United States Patent [19]

Cooper et al.

[11] 4,133,808

[45] Jan. 9, 1979

[54] 4-(FORMYLTHIO)AZETIDINONES AND OZONIZATION PROCESS THEREFOR

[75] Inventors: Robin D. G. Cooper; Douglas O. Spry, both of Indianapolis, Ind.

[73] Assignee: Eli Lilly and Company, Indianapolis, Ind.

[21] Appl. No.: 795,463

[22] Filed: May 10, 1977

Related U.S. Application Data

[62] Division of Ser. No. 626,946, Oct. 29, 1975, Pat. No. 4,048,157.

[51] Int. Cl.² .................. C07d 205/08; C07d 403/12; C07d 403/04
[52] U.S. Cl. ............................ 260/239 A; 260/326 S; 260/326.37; 544/16
[58] Field of Search .................. 260/239 A, 326 S

[56] References Cited

PUBLICATIONS

Chauvette et al., J. Amer. Chem. Soc. 96, (15); 4986–4987 (1974).

*Primary Examiner*—Mark L. Berch
*Attorney, Agent, or Firm*—Charles W. Ashbrook; Everet F. Smith

[57] ABSTRACT

Ozonolysis of 3-bromomethyl-2-cephem-4-carboxylic acid esters provides 1-(1-protected carboxy-2-hydroxy-3-bromo-1-propenyl)-3-amido(or imido)-4-formylthio-azetidin-2-ones, useful as intermediates in the preparation of cephalosporin antibiotics.

7 Claims, No Drawings

4-(FORMYLTHIO)AZETIDINONES AND OZONIZATION PROCESS THEREFOR

This is a division of application Ser. No. 626,946 filed Oct. 29, 1975, now U.S. Pat. No. 4,048,157.

BACKGROUND OF THE INVENTION

This invention relates to azetidinones which are useful in the preparation of 3-hydroxy cephalosporin derivatives. Several substituted azetidinones are currently known. An important utility for azetidinones is in the preparation of cephalosporin compounds which serve as intermediates for preparing cephalosporin antibacterial agents. For example, Nayler et al. converted benzyl 6β-(triphenylmethylamino)penicillinate into a 4-(3-phenylprop-2-ynylthio) azetidinone, which was subsequently converted to a 3-substituted methyl cephalosporin, as described in detail in *J. Chem. Soc. C* 58 (1973). Heusler et al., in U.S. Pat. No. 3,842,072, described certain 3-amido-4-(1,1-dimethyl-2-hydroxyethylthio)-azetidin-2-ones, prepared by reducing 3-hydroxy penams with a hydride reducing agent. Additionally, Kukolja et al. described a group of 3-chlorosulfinyl-3-imido-azetidin-4-ones which are useful for preparing desacetoxy cephalosporins; see U.S. Pat. No. 3,843,682.

Azetidin-2-ones substituted with 3-bromopropenyl and formylthio groups are hitherto unknown. The azetidinones currently available are not intermediates in the preparation of 3-hydroxy-3-cephems, an important class of cephalosporin compounds. An object of this invention is therefore to provide novel azetidin-2-ones, which compounds are especially useful for preparing 3-hydroxy-3-cephem compounds. An additional object of this invention is to provide a process for preparing 1-(1-protected carboxy-2-hydroxy-3-bromo-1-propenyl)-3-amido(or imido)-4-formylthio-azetidin-2-ones.

SUMMARY OF THE INVENTION

The subject of the present invention are azetidin2-ones, particularly 1-(1-protected carboxy-2-hydroxy3-bromo-1-propenyl)-3-amido(or imido)-4-formylthio-azetidin-2-ones having the formula

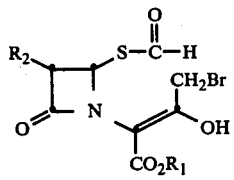

wherein $R_1$ represents a readily removable carboxylic acid protecting group which is substantially unreactive toward ozone; and $R_2$ represents phthalimido or a group having the formula $R_3$ CONH-, in which $R_3$ is hydrogen, $C_1$-$C_3$ alkyl, halomethyl, 4-protected-amino-4-protected-carboxybutyl, benzyloxy, 4-nitrobenzyloxy, tert.-butyloxy, 2,2,2-trichloroethoxy, 4-methoxybenzyloxy, or a group of the formula $R_4$—(O)-$_m$—$CH_2$— or

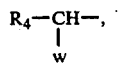

in which $R_4$ is phenyl or phenyl substituted with 1 or 2 halogens, protected hydroxy, nitro, cyano, trifluoromethyl, $C_1$-$C_4$ alkyl, $C_1$-$C_2$ alkoxy, m is 0 or 1, and w is protected hydroxy, protected carboxy or protected amino. An especially preferred group of azetidinones are those having the above formula when $R_2$ is phenylacetamido or phenoxyacetamido.

This invention additionally comprehends the process for preparing the azetidinone of the above formula which comprises ozonolyzing a 3-bromomethyl-2-cephem in an unreactive solvent at a temperature ranging from -100 to 0° C. to form an intermediate ozonide, and decomposing the ozonide by reaction with a mild reducing agent to provide the azetidinone of this invention.

DETAILED DESCRIPTION OF THE INVENTION

This invention provides new azetidinone compounds and a process for their preparation. More particularly, this invention provides azetidin-2-ones having the formula

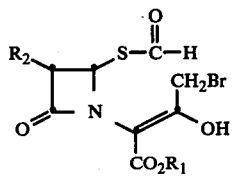

and a process for their preparation which comprises ozonolyzing a 3-bromomethyl-2-cephem of the formula

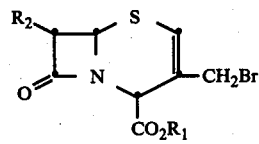

to form an intermediate ozonide, which upon decomposition in the presence of a mild reducing agent provides the corresponding 1-(1-protected carboxy-2-hydroxy-3-bromo-1-propenyl)-3-amido(or imido)-4-formylthio-azetidin-2-one of this invention.

In the above formulas, $R_1$ represents a carboxylic acid protecting group. The term refers to readily removable ester forming groups which do not appreciably react with ozone. For example, the protecting group should not possess isolated double or triple bonds which are known to be readily oxidized in the presence of ozone. Additionally, the carboxylic acid protecting group is preferably a residue of an ester group which is removable by routine methods, such as by reaction with dilute aqueous base; by reaction with an acid such as trifluoroacetic acid, hydrochloric acid, ptoluenesulfonic acid; by reaction with zinc in formic acid or acetic acid; or by hydrogenation in the presence of a palladium or rhodium catalyst on a suitable carrier. Any of a number of carboxylic acid protecting groups satisfy these conditions and many are well known and commonly used in the penicillin and cephalosporin arts. Typical examples of such protecting groups include among others the $C_4$-$C_6$ tert. alkyl groups, the benzyl, methoxybenzyl, and nitrobenzyl groups, the benzhydryl and phenacyl groups, and also the phthalimidomethyl and succinimidomethyl groups. Specific examples of $C_4$-$C_6$ tert.

alkyl groups include tert.-butyl, tert.-pentyl, and tert.-hexyl. Preferred protecting groups of the benzyl series include 3-methoxybenzyl, 4-methoxybenzyl, 4-nitrobenzyl, and 3,5-dimethoxybenzyl.

In the above formulas, $R_2$ represents an amido or imido group. The term imido includes cyclic imido groups such as succinimido, or preferably phthalimido. Amido groups are represented by the formula $$R_3-\overset{O}{\underset{\|}{C}}-NH-$$

in which $R_3$ is (1) hydrogen, $C_1$-$C_3$ alkyl, halomethyl, 4-protectedamino-4-protected carboxybutyl, benzyloxy, 4-nitrobenzyloxy, tert.-butyloxy, 2,2,2-trichloroethoxy, 4-methoxybenzyloxy;

(2) or a group having the formula $$R_4-(O)_m-CH_2-$$

in which m is 0 or 1, and $R_4$ is phenyl or phenyl substituted with 1 or 2 halogens, protected hydroxy, nitro, cyano, trifluoromethyl, $C_1$-$C_4$ alkyl, or $C_1$-$C_2$ alkoxy;

(3) or a group represented by the formula $$R_4-\underset{W}{\underset{|}{CH}}-$$

in which $R_4$ has the above defined meaning and W is a protected hydroxy, protected carboxy, or protected amino group.

In the above definitions of $R_3$, $C_1$-$C_3$ alkyl refers to methyl, ethyl, n-propyl and isopropyl. $C_1$-$C_4$ alkyl includes in addition to $C_1$-$C_3$ alkyl, n-butyl, isobutyl, and tert.-butyl. As used herein, "halo" includes fluorine, chlorine, bromine, and iodine. Typical examples of halomethyl groups therefore include fluoromethyl, chloromethyl, bromomethyl, and iodomethyl.

The term "protected amino" refers to any of a wide variety of groups which are used to protect an amino group during a chemical reaction in order to preclude undesired side reactions. In the instant invention, any amino protecting group which does not itself react with ozone can be employed. Typical examples of such amino protecting groups include acyl derivatives such as dichloroacetyl, 2-chloropropionyl, 3-phenylpropionyl, 4-chlorobutyryl; alkoxycarbonyl derivatives such as 2,2,2-trichloroethoxycarbonyl, tert.-butyloxycarbonyl, isobutyloxycarbonyl, cyclopentyloxycarbonyl, cyclohexyloxycarbonyl, 4-methoxybenzyloxycarbonyl, 4-nitrobenzyloxycarbonyl, diphenylmethoxycarbonyl; as well as alkyl and aryl derivatives, for instance benzyl and trityl, and the like.

"Protected carboxy" likewise refers to a group which can preclude reaction of the carboxy group during a chemical reaction, and which can easily be removed to regenerate the parent carboxy group. Carboxy protecting groups are well known and commonly used in the cephalosporin art, especially to protect the 4-carboxy group of a cephem. The most commonly used carboxy protecting groups are defined hereinbefore by $R_1$. Especially preferred carboxy protecting groups include tert.-butyl, benzhydryl, phenacyl, 4-nitrobenzyl, methoxybenzyl, and phthalimidomethyl.

The term "protected hydroxy" refers to readily cleavable groups which protect a hydroxyl group from undesired side reactions during a chemical modification elsewhere in the molecule. As with the other protecting groups described hereinbefore, the hydroxyl protecting group should be resistant to oxidation by ozone. Any of the commonly used hydroxyl protecting groups can be employed in the instant invention. Such commonly used groups include esters of carboxylic acids, especially formates, acetates, haloacetates, benzoates, 4-nitrobenzoates, methoxyacetates and phenoxyacetates. Alkoxycarbonyl derivatives of hydroxyl groups are also useful protecting groups. Examples of such alkoxycarbonyl protecting groups include ethoxycarbonyl, 2,2,2-trichloroethoxycarbonyl, isobutyloxycarbonyl, 2,2,2-tribromoethoxycarbonyl, 4-nitrophenoxycarbonyl, and related groups. Additionally, hydroxyl groups can be protected by conversion to an ether, such as the benzyl ether, benzhydryl ether, trityl ether, 4-nitrobenzyl ether, and the like.

Illustrative examples of groups represented by the formula $$R_3-\overset{O}{\underset{\|}{C}}-NH-$$

include: formamido, acetamido, propionamido, butyramdio, chloroacetamido, bromoacetamido, 4-tert.-butyoxycarbonylamino-4-(2,2,2-trichloroethoxycarbonyl) butylcarbonylamino, benzyloxycarbonylamino, tert.-butyloxycarbonylamino, and the like.

Specific examples of groups represented by the formula $$R_3-\overset{O}{\underset{\|}{C}}-NH-$$

when $R_3$ is a group having the formula $R_4-(O)_m-CH_2-$ include: phenoxyacetamido, phenylacetamido, 4-chlorophenylacetamido, 3,4-dibromophenylacetamido, 4,5-difluorophenoxyacetamido, 4-acetoxyphenylacetamido, 2-methoxyacetoxyphenoxyacetamido, 3-nitrophenylacetamido, 4-cyanophenoxyacetamido, 4-trifluoromethylphenoxyacetamido, 2-methylphenylacetamido, 3-ethylphenylacetamido, 4-tert.-butylphenylacetamido, 2-methoxyphenoxyacetamido, 3-ethoxyphenylacetamido, 4-methoxyphenylacetamido, and related groups.

$R_2$ can additionally be a group represented by the formula $$R_3-\overset{O}{\underset{\|}{C}}-NH-$$

in which $R_3$ is $$R_4-\underset{W}{\underset{|}{CH}}-,$$

typical examples of which include 2-phenyl-2-(tert.-butoxycarbonylamino)acetamido, 2-(4-chlorophenyl)-2-acetoxyacetamido, 2-(4-acetoxyphenyl)-2-(2,2,2-trichloroethoxycarbonylamino)acetamido, 2-(3,4-diiodophenyl)-2-tert.-butoxycarbonylacetamido, 2-(4-nitrophenyl)-2-(cyclohexyloxycarbonylamino)acetamido, 2-(4-cyanopheny)-2-(dichloroacetylamino)acetamido, 2-(2-n-butylphenyl)-2-(benzyhydryloxycarbonyl- )acetamido, 2-(3-methoxyphenyl)-2-(4-nitrobenzoyloxy)acetamido, and the like.

In accordance with the process of this invention, a 3-bromomethyl-2-cephem derivative is treated with ozone in an unreactive solvent at a temperature between $-100°$ and $0°$ C. to form an intermediate ozonide, which, when decomposed by reaction with a mild reducing agent, provides the novel azetidinone of the present invention. More particularly, a 7-amido(or imido)-3-bromomethyl-2-cephem-4-carboxylic acid ester is ozonolized, by reaction with ozonized oxygen, to form an intermediate ozonide involving the $C_2$-$C_3$ double bond of the $\Delta^2$-cephem. Treatment of the ozonide so formed with a mild reducing agent effects decomposition of the ozonide and provides the corresponding 1-(1-protected carboxy-2-hydroxy-3-bromo-1-propenyl)-3-amido(or imido)-4-formylthio-azetidin2-one. The ozonolysis of the 3-bromomethyl-2-cephem is generally carried out by passing ozonized oxygen gas through a solution of the 3-bromomethyl-2-cephem in an unreactive solvent. The reaction generally is carried out at a temperature below about $20°$ C., preferably at a temperature within the range of $-100$ to about $0°$ C. The double bond of the $\Delta^2$-cephem reacts preferentially with ozone to form, in situ, an intermediate ozonide, which generally is not isolated, but rather is decomposed while still in the reaction mixture to provide the azetidinone of this invention. At least a stoichiometric amount of ozone gas is generally employed, although slight excesses of ozone, an amount up to about 0.1 molar excess for instance, can be utilized if desired. Large excesses of ozone should be avoided, however, since over-oxidation of the cephem can occur. For example, the sulphur atom of the cephem ring system can react with ozone to form the corresponding sulfoxide. While sulfoxide formation can occur in the presence of large excesses of ozone, such oxidation proceeds at a very slow rate, whereas reaction of the $C_2$-$C_3$ cephem double bond with ozone occurs preferentially and proceeds very rapidly. The progress of the ozonolysis reaction generally is monitored to determined the relative amounts of the starting 3-bromomethyl-2-cephem and the corresponding ozonide intermediate being formed. For instance, the progress of the desired oxidation can be monitored chromatographically by withdrawing aliquot portions of the reaction mixture, decomposing the intermediate ozonide by adding to the aliquot portion an amount of a mild reducing agent, and then chromatographing the aliquot solution by thin layer chromatography. The amount of unreacted starting material remaining in the reaction mixture can be assessed by comparison of the thin layer chromatogram with that of a known amount of the starting material. The ozonolysis reaction is generally curtailed when no starting 2-cephem remains in the reaction mixture, thereby minimizing the possibilities for over oxidation. Generally, the reaction is substantially complete within 5 to 60 minutes; however, the precise length of reaction depends upon the amount of cephem being ozonolized. As hereinbefore indicated, the ozonolysis reaction is best conducted in an unreactive solvent. Any of a number of unreactive solvents can be employed for the reaction. Commonly used unreactive solvents include the halogenated hydrocarbons, such as chloroform, dichloromethane, fluorotrichloromethane, 1,2-dichloroethane, dichlorodifluoromethane, 1,1-dichloroethane, bromoethane, carbon tetrachloride, and the like. Additionally, ethers such as diethyl ether, petroleum ether, tetrahydrofuran, diethylene glycol dimethyl ether, methyl ethyl ether, and related ethers are suitable unreactive solvents. Similarly, solvents such as hexane, dimethylformamide, dimethylacetamide, ethyl acetate, methyl acetate, water, acetic acid, and the like, can be employed in the ozonolysis reaction.

Upon completion of the ozonolysis reaction, as evidence for example by the lack of any 3-bromomethyl-2-cephem remaining in the reaction mixture as shown by thin layer chromatographic analysis, any excess ozone remaining in the reaction mixture generally is removed by purging the reaction mixture with excess nitrogen or oxygen gas. The ozonide intermediate which is formed by ozonolysis of the $\Delta^2$-cephem normally is not isolated, but rather is decomposed by reaction with a mild reducing agent to provide the corresponding azetidinone of this invention. The term "mild reducing agent" as used herein refers to any reducing agent capable of decomposing the ozonide intermediate, while at the same time not affecting other sites of the ozonide molecule. For example, the reducing agent should not hydrolyze the azetidinone ring system under the reaction conditions being used. Mild reducing agents which commonly are used when decomposing ozonides are well known, and include such agents as zinc or magnesium and water or acetic acid, sodium bisulfite, sulfur dioxide, catalytic reduction, trimethyl phosphite, stannous chloride, zinc metal dust, Raney nickel, dimethylsulfide and the like. The decomposition of the intermediate ozonide is normally accomplished by simply adding an excess of a reducing agent to the reaction mixture, and stirring the mixture at a temperature ranging from about $-80$ to $0°$ C. The decomposition reaction is generally complete within about 5 to 60 minutes, or alternatively, the reaction is complete when the reaction mixture is negative to a potassium iodide-starch test.

The azetidin-2-one thus formed typically is isolated by washing the reaction mixture with water. The organic phase is separated therefrom and concentrated to dryness, and if desired, additional quantities of the product azetidinone can be extracted from the aqueous phase into a water-immiscible solvent such as dichloromethane, ethyl acetate, diethyl ether, or the like. The azetidinone so formed can be further purified if desired by any of a number of commonly used purification techniques, including column chromatography, gas chromatography, crystallization, and related methods.

It will be of course be understood by those skilled in the art of organic chemistry that the 1-(1-protected carboxy-2-hydroxy-3-bromo-1-propenyl)azetidin-2-ones of this invention are characterized as being enols which exist in tautomeric equilibrium with the corresponding 1,3-dicarbonyl ketone. The tautomeric equilibrium involving the azetidinone of this invention can be illustrated by the following generalized scheme:

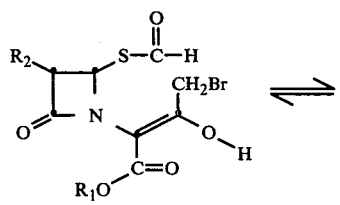

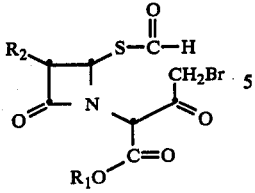

As a result of the existence of this tautomeric equilibrium, when reference is made herein to the 1-(1-protected carboxyl-2-hydroxy-3-bromo-1-propenyl-)azetidin-2-one of this invention, the tautomeric keto form of the molecule will be understood to be included therein.

The ozone gas which is required for the abovedescribed ozonolysis process can be prepared by means of an ozone generator of the type routinely used in synthetic and analytical chemical work to produce ozone by the action of an electric discharge on oxygen. One such ozone generator is that manufactured by the Welsback Corporation. The ozone is generated in a stream of oxygen gas which is then passed directly into the reaction mixture. The percentage of ozone contained in the oxygen stream can be varied as desired, for instance by varying the rate of flow of oxygen through the ozonizer, or by varying the intensity of the electric discharge. The concentration of ozone contained in the oxygen stream is not critical, since the progress of the reaction is monitored, for example by thin layer chromatography as described hereinbefore. The length of reaction time therefore is dependent in part upon the concentration of ozone going into the reaction mixture. For example, shorter reaction times can be realized when the concentration of ozone is relatively high, such as 14 to 15 percent for instance. Preferably, however, the ozone concentration is maintained at about 1 to 2 percent, thereby reducing the possibility of over-oxidation, although at the same time requiring somewhat longer reaction times for complete ozonolysis.

Typical examples of 1-(1-protected carboxy-2-hydroxy-3-bromo-1-propenyl)-3-amido(or imido)-4-formylthioazetidin-2-ones prepared by the present process and provided by this invention include:

1-(1-tert. butyloxycarbonyl-2-hydroxy-3-bromo-1-propenyl)-3-phenoxyacetamido-4-formylthio-azetidin-2-one;
1-(1-(4-nitrobenzyl)oxycarbonyl-2-hydroxy-3-bromo-1-propenyl)-3-phenylacetamido-4-formylthio-azetidin-2-one;
1-(1-succinimidomethyloxycarbonyl-2-hydroxy-3-bromo-1-propenyl)-3-phthalimido-4-formylthio-azetidin-2-one;
1-(1-benzyloxycarbonyl-2-hydroxy-3-bromo-1-propenyl)-3-(2,2,2-trichloroethoxycarbonyl)amino-4-formylthioazetidin-2-one;
1-(1-diphenylmethyloxycarbonyl-2-hydroxy-3-bromo-1-propenyl)-3-(3,5-dichlorophenoxy)acetamido-4-formylthio-azetidin-2-one;
1-(1-phenacyloxycarbonyl-2-hydroxy-3-bromo-1-propenyl)-3-(3-trifluoromethylphenyl)acetamido-4-formylthio-azetidin-2-one;
1-(1-tert.-pentyloxycarbonyl-2-hydroxy-3-bromo-1-propenyl)-3-(2-isopropylphenoxy)acetamido-4-formylthioazetidin-2-one;
1-(1-tert.-butyloxycarbonyl-2-hydroxy-3-bromo-1-propenyl)-3-phenylacetamido-4-formylthio-azetidin-2-one;
1-(1-(4-methoxybenzyl)oxycarbonyl-2-hydroxy-3-bromo-1-propenyl)-3-[2-(4-acetoxyphenyl)-2-tert.-butoxycarbonyl-amino]acetamido-4-formylthio-azetidin-2-one;
1-(1-(3-methoxybenzyloxycarbonyl)-2-hydroxy-3-bromo-1-propenyl)-3-[2-(3,5-dibromophenyl)-2-formyloxy]acetamido-4-formylthio-azetidin-2-one;
1-(1-phthalimidomethyloxycarbonyl-2-hydroxy-3-bromo-1-propenyl)-3-formamido-4-formylthio-azetidin-2-one;
1-(1-tert.-hexyloxycarbonyl-2-hydroxy-3-bromo-1-propenyl)-3-bromoacetamido-4-formylthio-azetidin-2-one;
1-(1-benzyloxycarbonyl-2-hydroxy-3-bromo-1-propenyl)-3-(4-cyclopentyloxycarbonylamino-4-diphenylmethyloxycarbonyl)butyramido-4-formylthio-azetidin-2-one;
1-(1-tert.-butyloxycarbonyl-2-hydroxy-3-bromo-1-propenyl)-3-(4-methoxyphenyl)acetamido-4-formylthioazetidin-2-one;
1-(1-diphenylmethyloxycarbonyl-2-hydroxy-3-bromo-1-propenyl)-3-[2-(2-n-butylphenyl)-2-benzyloxycarbonyl] acetamido-4-formylthio-azetidin-2-one;
1-(1-succinimidomethyloxycarbonyl-2-hydroxy-3-bromo-1-propenyl)-3-[2-(4-cyanophenyl)-2-tert.-butoxycarbonylamino]acetamido-4-formylthio-azetidin-2-one;
1-(1-tert.-pentyloxycarbonyl-2-hydroxy-3-bromo-1-propenyl)-3-phenylacetamido-4-formylthio-azetidin-2-one;
1-(1-phthalimidomethyloxycarbonyl-2-hydroxy-3-bromo-1-propenyl)-3-[2-(4-(2,2,2-tribromoethoxycarbonyloxy) phenyl-2-acetoxy]acetamido-4-formylthio-azetidin-2-one;
1-(1-(4-methoxybenzyl)oxycarbonyl-2-hydroxy-3-bromo-1-propenyl)-3-propionamido-4-formylthio-azetidin-2-one;
1-(1-diphenylmethyloxycarbonyl-2-hydroxy-3-bromo-1-propenyl)-3-[2-(3,5-difluorophenyl)-2-dichloroacetamido]acetamido-4-formylthio-azetidin-2-one;
1-(1-tert.-butyloxycarbonyl-2-hydroxy-3-bromo-1-propenyl)-3-[2-(4-trifluoromethylphenyl)-2-tert.-butyloxycarbonyl)acetamido]-4-formylthio-azetidin-2-one;
1-(1-tert.-hexyloxycarbonyl-2-hydroxy-3-bromo-1-propenyl)-3-[2-(2-ethoxyphenyl)-2-benzoyloxy)acetamido]-4-formylthio-azetidin-2-one;
1-(1-tert.-butyloxycarbonyl-2-hydroxy-3-bromo-1-propenyl)-3-[2-(2,3-difluorophenyl)-2-trichloroacetoxy] acetamido-4-formylthio-azetidin-2-one;
1-(1-(4-nitrobenzyl)oxycarbonyl-2-hydroxy-3-bromo-1-propenyl)-3-[2-(2-cyanophenyl)-2-(4-nitrobenzyloxycarbonyl)amino]acetamido-4-formylthio-azetidin-2-one;
1-(1-(3,5-dimethoxybenzyl)oxycarbonyl-2-hydroxy-3-bromo-1-propenyl)-3-[2-(4-formyloxyphenyl)-2-(4-methoxybenzyloxycarbonyl)amino]acetamido-4-formylthio-azetidin2-one;
1-(1-tert.-butyloxycarbonyl-2-hydroxy-3-bromo-1-propenyl)-3-[2-(3-isobutylphenyl)-2-formyloxy]acetamido-4-formylthio-azetidin-2-one;

1-(1-(3-methoxybenzyl)oxycarbonyl-2-hydroxy-3-bromo-1-propenyl)-3-(4-cyanophenoxy)acetamido-4-formylthioazetidin-2-one;

1-(1-(4-nitrobenzyl)oxycarbonyl-2-hydroxy-3-bromo-1-propenyl)-3-(2,2,2-trichloroethoxycarbonyl)amino-4-formylthio-azetidin-2-one;

1-(1-phenacyloxycarbonyl-2-hydroxy-3-bromo-1-propenyl)-3-fluoroacetamido-4-formylthio-azetidin-2-one; and the like.

As hereinbefore pointed out, the starting materials required for the preparation of the azetidinones of this invention are 3-bromomethyl-2-cephem-4-carboxylates. These Δ²-cephems are readily prepared by brominating the corresponding 3-methyl-2-cephem-4-carboxylate. For example, reaction of a 3-methyl-2-cephem with N-bromosuccinimide effects bromination of the 3-methyl group and provides the corresponding 3-bromomethyl-2-cephem. These 3-bromomethyl-2-cephem-4-carboxylates are described more fully by Webber et al. in U.S. Pat. No. 3,637,678.

The azetidin-2-ones provided by this invention are useful as intermediates in the preparation of 3-hyroxy cephalosporin antibiotics. In particular, a 1-(1-protectedcarboxy-2-hydroxy-3-bromo-1-propenyl)-3-amido(or imido)-4-formylthio-azetidin-2-one of this invention can readily be cyclized to provide the corresponding 7-amido (or imido)-4-protected-carboxy-3-hydroxy-3-cephem. Such cyclization of the azetidinone is effected by reaction with a cyclizing agent, such as for example 1,5-diazobicyclo[5.4.0]undec-5-ene (DBU) or mercuric acetate. As an example, 1-(1-tert.-butyloxycarbonyl-2-hydroxy-3-bromo-1-propenyl)-3-phenoxyacetamido-4-formylthio-azetidin-2-one can be treated with DBU in a suitable solvent, for instance dichloromethane, thereby effecting a cyclization of the azetidinone to provide tert.-butyl 7-phenoxyacetamido- 3-hydroxy-3-cephem-4-carboxylate.

The 3-hydroxy-Δ³-cephalosoporins so formed are useful as antibiotics or as intermediates in the preparation of useful antibacterial agents. For example, removal of any protecting groups utilized throughout the molecule provides a 3-hydroxy-Δ³-cephem-4-carboxylic acid, which compound is a potent antibiotic. Additionally, a 3-hydroxy-3-cephem-4-carboxylic acid ester can be alkylated at the 3-hydroxy group to provide a 3-alkoxy-3-cephem-4-carboxylic acid ester, which, when converted to the unprotected acid by general methods, are valuable antibiotics. For instance, 4-nitrobenzyl 7-phenoxyacetamido-3-hydroxy-3-cephem-4-carboxylate can be treated with an alkylating agent such as methyl fluorosulfonate, in the presence of a base as potassium tert.-butoxide, thereby providing the corresponding 4-nitrobenzyl 7-phenoxyacetamido-3-methoxy-3-cephem-4-carboxylate. Normal ester cleavage, for instance hydrogenolysis in the presence of palladium on charcoal, provides 7-phenoxyacetamdio-3-methoxy-3-cephem-4-carboxylic acid, a potent antibacterial agent.

Additionally, the 3-hydroxy-3-cephem prepared from the azetidinone of this invention can be converted to a 3-chloro-3-cephem-4-carboxylic acid ester. Removal of protecting groups from the 3-chloro derivative provides the corresponding 3-chloro-3-cpehem-4-carboxylic acid, a potent antibiotic. As an example, reaction of tert.-butyl 7-phenoxyacetamido-3-hydroxy-3-cephem-4-carboxylate with phosphorous trichloride provides the corresponding 3-chloro derivative. Removal of the carboxyl protecting group, for instance by reaction with trifluoroacetic acid, provides 7-phenoxyacetamido-3-chloro-3-cephem-4-carboxylic acid.

In order to more fully illustrate various aspects of this invention, the following detailed examples are presented. While the examples represent specific embodiments of the invention, they should not be construed as limiting the scope of the invention in any respect.

EXAMPLE 1

1-(1-tert.-butyloxycarbonyl-2-hydroxy-3-bromo-1-propenyl)-3-phenoxyacetamido-4-formylthio-azetidin-2-one A solution of 5 g. of tert. butyl 7-phenoxyacetamido-3-bromomethyl-2-cephem-4-carboxylate in 150 ml. of dichloromethane was stirred and cooled to −80° C. in a dry ice-acetone bath. Ozonized oxygen gas was bubbled into the reaction mixture for about 20 minutes, at which time no starting cephalosporin remained in the reaction mixture, as shown by thin layer chromatographic analysis. The reaction mixture was purged of the remaining ozone by passing nitrogen gas through the solution for 5 minutes. The reaction mixture was stirred for 20 minutes with 50 ml. of saturated aqueous sodium bisulfite solution. The organic layer was separated, washed with water, dried, and the solvent was removed under reduced pressure, providing 1-(-tert.-butyloxycarbonyl-2-hydroxy-3-bromo-1-propenyl)-3-phenoxyacetamido-4-formylthio-azetidin-2-one as an oil.

NMR (CDCl$_3$):

δ 1.42 (s, 9H, —C(CH$_3$)$_3$)

δ 4.18 (d, 2H, —CH$_2$Br)

δ 4.52 (s, 2H, —OCH$_2$CON)

δ 5.19 (dd, 1H, C$_3$—H)

δ 6.10 (d, 1H, C$_4$—H)

δ 6.75–7.50 (m, 6H, aromatic and NH)

δ 10.0 (s, 1H, aldehydic proton)

δ 12.42 (s, 1H, enolic proton)

EXAMPLE 2

1-(1-(4-nitrobenzyl)oxycarbonyl-2-hydroxy-3-bromo-1-propenyl)-3-(2-phenyl-2-tert.-butyoxycarbonylamino)acetamido-4-formylthio-azetidin-2-one A solution of 2 g. of 4-nitrobenzyl 7-(2-phenyl-2-tert.-butoxycarbonylamino)acetamido-3-bromomethyl-2-cephem-4-carboxylate in 100 ml. of chloroform was stirred at −78° C. in a dry ice-acetone bath while ozone gas was bubbled through the solution. Thin layer chromatography indicated that all of the starting 3-bromomethyl-2-cephem was consumed after 10 minutes, at which time the addition of ozone was stopped. Nitrogen gas was bubbled through the reaction mixture for 5 minutes in order to purge the solution of any excess ozone that was present. The reaction mixture was stirred for 10 minutes while sulfur dioxide was bubbled through the solution, at which time the reaction mixture gave a negative potassium iodide-starch test. The solvent was removed from the reaction mixture under reduced pressure, providing an oil which was shown to be 1-(1-(4-nitrobenzyl)oxycarbonyl-2-hydroxy-3-bromo-1-propenyl)-3-(2-phenyl-2-tert.-butoxycarbonylamino)acetamido-4-formylthio-azetidin-2-one.

EXAMPLE 3

1-(1-phthalimidomethyloxycarbonyl-2-hydroxy-3-bromo-1-propenyl)-3-(4-isopropylphenoxy)acetamido-4-formylthio-azetidin-2-one A solution of 1 g. of phthalimidomethyl 7-(4-isopropylphenoxy)-acetamido-3-bromomethyl-2-cephem-4-carboxylate in 100 ml. of ethyl acetate was stirred and cooled to −65° C. in a dry ice-acetone bath. Ozone was bubbled through the reaction solution for 5 minutes, at which time no starting 3-bromomethyl-2-cephem remained in the reaction mixture, as demonstrated by thin layer chromatography. Oxygen was bubbled through the reaction mixture for 5 minutes to purge the solution of any excess ozone remaining in the mixture. After the solution was purged of excess ozone, 5 g. of trimethylphosphite was added to the reaction mixture, and the solution was stirred for 20 minutes. The solution was next washed with water, dried, and the solvent was removed under reduced pressure to afford 1-(1-phthalimidomethyloxycarbonyl-2-hydroxy-3-bromo-1-propenyl)-3-(4-isopropylphenoxy)acetamido-4-formylthio-azetidin-2-one.

EXAMPLE 4

1-(1-tert.-pentyloxycarbonyl-2-hydroxy-3-bromo-1-propenyl)-3-phenylacetamido-4-formylthio-azetidin-2-one A solution of 2 g. of tert. pentyl 7-phenylacetamido-3-bromomethyl-2-cephem-4-carboxylate in 150 ml. of dichloromethane was stirred at −74° C. while ozone was bubbled into the solution for 10 minutes. The reaction mixture was then purged of any excess ozone by passing nitrogen through the reaction solution, and 5 g. of dimethylsulfide was added. The reaction mixture was stirred for 30 minutes at −60° C. and then washed with water, dried, and the solvent was removed therefrom under reduced pressure to provide 1-(1-tert.-pentyloxycarbonyl-2-hydroxy-3-bromo-1-propenyl)-3-phenylacetamido-4-formylthio-azetidin-2-one.

EXAMPLE 5

Preparation of tert.-butyl 7-phenoxyacetamido-3-hydroxy-3-cephem-4-carboxylate

To a solution of 391 mg. of mercuric acetate in 15 ml. of dichloromethane containing 15 ml. of acetic acid was added in one portion 435 mg. of 1-(1-tert.-butyloxycarbonyl-2-hydroxy-3-bromo-1-propenyl)-3-phenoxyacetamido-4-formylthio-azetidin-2-one. The reaction mixture was stirred at room temperature for 5 minutes, and then hydrogen sulfide gas was bubbled into the reaction mixture for 1 minute. The reaction mixture was filtered through a filter aid and charcoal. The filtrate was evaporated to dryness under reduced pressure to provide tert.-butyl 7-phenoxyacetamido-3-hydroxy-3-cephem-4-carboxylate.

We claim:

1. A process for preparing a compound of the formula

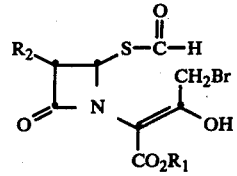

wherein:
$R_1$ is a readily removable carboxylic acid protecting group which is substantially unreactive toward ozone; and
$R_2$ is phthalimido or a group having the formula

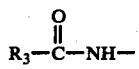

wherein:
$R_3$ is
(1) hydrogen, $C_1$-$C_3$ alkyl, halomethyl, benzyloxy, 4-nitrobenzyloxy tert.-butyloxy, 2,2,2-trichloroethoxy, 4-methoxybenzyloxy, 4-protected amino-4-protected carboxybutyl in which the amino protecting group and carboxy protecting group are substantially unreactive toward ozone; or
(2) a group of the formula

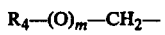

wherein:
m is 0 or 1; and
$R_4$ is phenyl or phenyl substituted with 1 or 2 halogens, nitro, cyano, trifluoromethyl, $C_1$-$C_4$ alkyl, $C_1$-$C_2$ alkoxy, protected hydroxy in which the hydroxy protecting group is substantially unreactive toward ozone; or
(3) a group of the formula

wherein:
$R_4$ is as defined above and
W is protected hydroxy, protected carboxy, or protected amino in which the hydroxy protected group, the carboxy protecting group and the amino protecting group are substantially unreactive toward ozone;
comprising the steps of reacting ozone with a compound of the formula

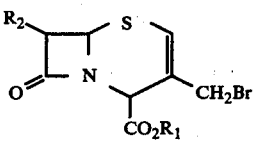

in an unreactive solvent at a temperature ranging from −100 to about 0° C. to form an intermediate ozonide, and reacting the ozonide with a mild reducing agent.

2. The process according to claim 1 wherein $R_1$ is $C_4$-$C_6$ tert. alkyl, benzyl, nitrobenzyl, methoxybenzyl, benzhydryl, phenacyl, phthalimidomethyl, or succinimidomethyl.

3. The process according to claim 2 wherein $R_2$ is selected from phenoxyacetamido and phenylacetamido.

4. The process according to claim 1 wherein the reaction temperature is from about $-80°$ C. to $0°$ C.

5. The process according to claim 4 wherein the unreactive reaction solvent is selected from halogenated hydrocarbons.

6. The process according to claim 5 wherein the mild reducing agent is selected from sodium bisulfite, sulfur dioxide, trimethyl phosphite, stannous chloride, zinc metal dust, Raney nickel, and dimethylsulfide.

7. The process according to claim 6, said process comprising reacting tert.butyl 7-phenoxyacetamido-3-bromomethyl-2-cephem-4-carboxylate with ozone at about 31 80° C. in dichloromethane to form an intermediate ozonide, and decomposing the ozonide by reaction with sodium bisulfite to form 1-(1-tert. butyloxycarbonyl-2-hydroxy-3-bromo-1-propenyl)-3-phenoxyacetamido-4-formylthio-azetidin-2-one.

* * * * *